United States Patent
Gulotta et al.

(10) Patent No.: US 12,409,406 B2
(45) Date of Patent: *Sep. 9, 2025

(54) COLLECTING A GASEOUS POLLUTANT FROM AIR

(71) Applicant: MOVA Technologies, Inc., Pulaski, VA (US)

(72) Inventors: Matthew F. Gulotta, Mount Airy, MD (US); Jonathan M. Hager, Salem, VA (US); Christian M. James, Blacksburg, VA (US)

(73) Assignee: MOVA Technologies, Inc., Pulaski, VA (US)

( * ) Notice: Subject to any disclaimer, the term of this patent is extended or adjusted under 35 U.S.C. 154(b) by 104 days.

This patent is subject to a terminal disclaimer.

(21) Appl. No.: 17/745,082

(22) Filed: May 16, 2022

(65) Prior Publication Data

US 2023/0091976 A1     Mar. 23, 2023

Related U.S. Application Data

(63) Continuation of application No. 17/482,009, filed on Sep. 22, 2021, now Pat. No. 11,331,619.

(51) Int. Cl.
*B01D 53/02*     (2006.01)
*A01K 1/00*     (2006.01)
(Continued)

(52) U.S. Cl.
CPC ........ *B01D 53/0446* (2013.01); *A01K 1/0052* (2013.01); *A61L 9/014* (2013.01);
(Continued)

(58) Field of Classification Search
CPC ............ A01K 1/0052; A61L 2209/111; A61L 2209/14; A61L 2209/22; A61L 9/014;
(Continued)

(56) References Cited

U.S. PATENT DOCUMENTS 2,583,352 A    1/1952  Berg
2,636,575 A    4/1953  Watson
(Continued)

OTHER PUBLICATIONS

Krause, K.-H., et al., "Measuring and Simulation of the Distribution of Ammonia in Animal Houses", [no date], 13 pages.
(Continued)

*Primary Examiner* — Christopher P Jones
(74) *Attorney, Agent, or Firm* — Sheppard Mullin Richter & Hampton LLP

(57) ABSTRACT

An apparatus for collecting a gaseous pollutant from air may comprise multiple vertical panel-beds each containing a solid sorbent; a fan to pass the air through the multiple vertical panel-beds and over the solid sorbent; an outlet gate configured to release the solid sorbent from the multiple vertical panel-beds after the fan passes the air over the solid sorbent; a regeneration vessel configured to regenerate the released solid sorbent by recovering the gaseous pollutant from the released solid sorbent; and a conveyor configured to return the regenerated solid sorbent to the multiple vertical panel-beds.

19 Claims, 6 Drawing Sheets

(51) Int. Cl.
*A61L 9/014* (2006.01)
*B01D 53/04* (2006.01)
*B01J 20/10* (2006.01)
*B01J 20/18* (2006.01)
*B01J 20/22* (2006.01)
*B01J 20/26* (2006.01)
*B01J 20/28* (2006.01)
*B01J 20/34* (2006.01)

(52) U.S. Cl.
CPC .............. *B01J 20/103* (2013.01); *B01J 20/18* (2013.01); *B01J 20/226* (2013.01); *B01J 20/26* (2013.01); *B01J 20/28052* (2013.01); *B01J 20/34* (2013.01); *A61L 2209/111* (2013.01); *A61L 2209/14* (2013.01); *A61L 2209/22* (2013.01); *B01D 2253/102* (2013.01); *B01D 2253/108* (2013.01); *B01D 2253/202* (2013.01); *B01D 2253/204* (2013.01); *B01D 2253/206* (2013.01); *B01D 2257/304* (2013.01); *B01D 2257/402* (2013.01); *B01D 2257/406* (2013.01); *B01D 2257/502* (2013.01); *B01D 2257/504* (2013.01); *B01D 2257/7025* (2013.01); *B01D 2259/40088* (2013.01)

(58) Field of Classification Search
CPC ........ B01D 2253/102; B01D 2253/106; B01D 2253/108; B01D 2253/202; B01D 2253/204; B01D 2253/206; B01D 2253/25; B01D 2257/304; B01D 2257/402; B01D 2257/406; B01D 2257/502; B01D 2257/504; B01D 2257/7025; B01D 2258/0266; B01D 2259/40088; B01D 53/0446; B01D 53/06; B01J 20/103; B01J 20/18; B01J 20/226; B01J 20/26; B01J 20/28052; B01J 20/34; Y02C 20/10; Y02C 20/20; Y02C 20/40
See application file for complete search history.

(56) References Cited

U.S. PATENT DOCUMENTS

| | | | |
|---|---|---|---|
| 2,808,367 A | 10/1957 | Bergstrom | |
| 3,964,890 A * | 6/1976 | Bonn | G21F 9/02 376/314 |
| 4,255,403 A | 3/1981 | Mayer | |
| 4,405,354 A | 9/1983 | Thomas, II | |
| 5,026,528 A * | 6/1991 | Gal | C01B 17/20 422/111 |
| 5,308,590 A * | 5/1994 | Kersey | B01D 46/32 95/110 |
| 5,332,562 A | 7/1994 | Kersey | |
| 5,346,674 A | 9/1994 | Weinwurm | |
| 6,126,722 A | 10/2000 | Mitchell | |
| 8,071,342 B2 | 12/2011 | Herrema | |
| 8,679,414 B2 | 3/2014 | Miya | |
| 8,906,332 B2 | 12/2014 | Szogi | |
| 10,994,241 B1 | 5/2021 | Junaedi | |
| 11,331,619 B1 | 5/2022 | Gulotta | |
| 2006/0054023 A1 | 3/2006 | Raetz | |
| 2006/0081194 A1 | 4/2006 | Aylen | |
| 2009/0301402 A1 | 12/2009 | Devine | |
| 2012/0213675 A1 | 8/2012 | Chyou | |
| 2015/0010452 A1 | 1/2015 | Elliott | |
| 2021/0093993 A1 | 4/2021 | Strand | |
| 2021/0236983 A1 | 8/2021 | Junaedi | |

OTHER PUBLICATIONS

Lahav, Ori, et al., "A New Approach for Minimizing Ammonia Emissions from Poultry Houses", Water, Air, and Soil Pollution, vol. 191, doi:10.1007/s11270-008-9616-0, Jun. 2008 (Year: 2008), pp. 183-197.

Melse, Roland W., et al., "Air Treatment Techniques for Abatement of Emissions from Intensive Livestock Production", The Open Agriculture Journal, vol. 3, (Year: 2009), pp. 6-12.

Miles, D. M., "Vertical Stratification of Ammonia in a Broiler House", Journal of Applied Poultry Research, vol. 17, No. 3, doi:10.3382/japr.2007-00113, (Year: 2008), pp. 348-353.

Miles, D. M., et al., Atmospheric Ammonia is Detrimental to the Performance of Modern Commercial Broilers. Poultry Science, vol. 83, No. 10, doi:10.1093/ps/83.10.1650), (Year: 2004), pp. 1650-1654.

Moore, Philip, et al., "Reducing Ammonia Emissions from Poultry Litter with Alum", Mitigating Air Emissions from Animal Feeding Operations Conference, May 2008 (Year: 2008), 5 pages.

National Emission Inventory-Ammonia Emissions from Animal Husbandry Operations (Draft Report), United States Environmental Protection Agency, Jan. 30, 2004 (Year: 2004), 131 pages.

Takahashi, Akira, et al., "Trace Ammonia Removal from Air by Selective Adsorbents Reusable with Water", ACS Applied Materials & Interfaces, vol. 12, No. 13, doi:10.1021/acsami.9b22384, (Year: 2020), pp. 15115-15119.

Wathes, C. M., et al., "Concentrations and Emission Rates of Aerial Ammonia, Nitrous Oxide, Methane, Carbon Dioxide, Dust and Endotoxin in UK Broiler and Layer Houses", British Poultry Science, vol. 38, No. 1, doi:10.1080/00071669708417936, (Year: 1997), pp. 14-28.

Wheeler, Eileen E., Detecting Ammonia in Poultry Housing Using Inexpensive Instruments, Jul. 6, 2021 (Year: 2021), 5 pages.

Zhou, Ying, et al., "Effects of Ammonia Exposure on Growth Performance and Cytokines in the Serum, Trachea, and Ileum of Broilers", Poultry Science, vol. 99, No. 5, doi:10.1016/j.psj.2019.12.063, (Year: 2020), pp. 2485-2493.

* cited by examiner

COLLECTING A GASEOUS POLLUTANT FROM AIR

CROSS REFERENCE TO RELATED APPLICATIONS

The present application is a continuation of U.S. patent application Ser. No. 17/482,009, filed Sep. 22, 2021, entitled "COLLECTING A GASEOUS POLLUTANT FROM AIR WITHIN AN ANIMAL ENCLOSURE," the disclosure thereof incorporated by reference herein in its entirety.

DESCRIPTION OF RELATED ART

The disclosed technology relates to the removal and recovery of gaseous pollutants such as ammonia and/or $CO_2$, from agriculture facilities to reduce atmospheric emissions and improve indoor air quality.

BACKGROUND

Concentrated animal feeding operations (CAFO) continue to proliferate as the global demand for low-cost protein increases. Modern advances in CAFO technology have allowed growers to manage a large number of animals on a single farm, which has exacerbated pollutant emissions and their resulting environmental impact. These operations produce large amounts of pollutants such as hydrogen sulfide, methane, nitrous oxide, carbon dioxide, particulate matter, and especially ammonia, which can produce undesirable odors, cause health concerns, and contribute to negative climate effects. CAFO's are now the leading cause of ammonia emissions and have been linked to the degradation of water resources and detrimental health effects of both animals and human workers. Ammonia is produced from the microbial decomposition of nitrogen-containing organic compounds in animal manure and by the hydrolysis of uric acid (Lahav, O., Mor, T., Heber, A. J., Molchanov, S., Ramirez, J. C., Li, C., & Broday, D. M. (2008). A New Approach for Minimizing Ammonia Emissions from Poultry Houses. *Water, Air, and Soil Pollution,* 191(1-4), 183497. doi:10.1007/s11270-008-9616-0). Specifically, poultry farming now causes the most ammonia emissions of any CAFO (30%) (National Emission Inventory—Ammonia Emissions from Animal Husbandry Operations (Rep.), 2004, United States Environmental Protection Agency.) These ammonia emissions are of major environmental concern to the Chesapeake Bay and other waterways. Ammonia's highly soluble nature leads to contaminated runoff and over-nitrification of water bodies, which is now severely degrading water quality and aquatic habitat.

In poultry production, high concentrations of ammonia are linked to decreased bird performance (e.g., reduced bird weight) and health concerns (e.g., Newcastle disease and respiratory problems). Studies have shown that at elevated levels of ammonia of 50 ppm and 75 ppm, bird weight was reduced by 6% and 9%, respectively. Furthermore, ammonia levels above 25 ppm have been linked to increase bird mortality. In poultry houses, ammonia concentrations often rise above 50 ppm, especially during low-ventilation periods and when the same litter is utilized for multiple flocks (Miles, D., Branton, S., & Lott, B. (2004). Atmospheric Ammonia is Detrimental to the Performance of Modern Commercial Broilers. *Poultry Science,* 83(10), 1650-1654. doi:10.1093/ps/83.10.1650). A recent study also examined the same topic and yielded results consistent with the aforementioned study (Zhou et al., 2020, Effects of ammonia exposure on growth performance and cytokines in the serum, trachea, and ileum of broilers. Poultry Science, 99(5), 2485-2493. doi:10.1016/j.psj.2019.12.063).

Thus far, ventilation in buildings has been the primary method to reduce gaseous pollutant concentrations. However, ventilation rates are dictated by temperature and moisture levels in the building, and not by pollutant levels, meaning pollutant removal is simply a byproduct of ventilation. In the winter and during brooding periods, ventilation rates are lower which leads to increased ammonia concentrations in the building. When unacceptable levels are reached, ventilation rates are increased to reduce concentrations. However, this causes excessive heat loss and increases heating costs, especially in colder weather. Furthermore, the practice of simply exhausting pollutants negatively impacts the environment and contributes to climate change and is, therefore, no longer a desirable practice. A study identified similar trends in the concentrations of other pollutants (i.e., particulate matter, methane, etc.) which have also been linked to detrimental health effects in animals and workers. The study suggests filtering pollutants such as particulate matter can improve indoor air quality and bird production (Wathes, C. M., Holden, M. R., Sneath, R. W., White, R. P., & Phillips, V. R. (1997). Concentrations and emission rates of aerial ammonia, nitrous oxide, methane, carbon dioxide, dust and endotoxin in UK broiler and layer houses. *British Poultry Science,* 38(1), 14-28. doi:10.1080/00071669708417936).

In the U.S., the eight-hour exposure limit to ammonia for humans has been set at 25 ppm by the National Institute of Occupational Safety and Health, and to 50 ppm by the Occupational Safety and Health Administration. However, growers often do not have ammonia monitors to determine concentrations and instead rely on their senses to determine when levels have become unacceptable. However, workers often develop a decreased sensitivity to ammonia levels and become unable to detect ammonia until levels are dangerously high (Wheeler, E. E. (2021, July 06). Detecting Ammonia in Poultry Housing Using Inexpensive Instruments). Furthermore, the ammonia concentration in poultry houses has been found to decrease as height from litter increases, and is often much lower at worker height. This can cause an incorrect sense of ammonia levels by workers at bird level, further driving decreased production performance. In one study that examined ammonia concentrations in layer houses, studies found that the ammonia levels at the surface of the litter were as high as 170 ppm and decreased to ambient levels (20 ppm) above 20 cm (bird height) (Lahav, O., Mor, T., Heber, A. J., Molchanov, S., Ramirez, J. C., Li, C., & Broday, D. M. (2008). A New Approach for Minimizing Ammonia Emissions from Poultry Houses. *Water, Air, and Soil Pollution,* 191(1-4), 183-197. doi:10.1007/s11270-008-9616-0). In broiler houses, a study found that concentrations at the surface of new litter were more than double of those at the height of the workers. This same study also found that ammonia concentrations on built-up litters were over double of those on brand-new litters (Miles, D. (2008). Vertical Stratification of Ammonia in a Broiler House. *Journal of Applied Poultry Research,* 17(3), 348-353. doi:10.3382/japr.2007-00113). A third study validated this profile in broiler houses and found rapidly decreasing ammonia concentrations above bird height (Krause, K. H., & Janssen, J. (n.d.). Measuring and simulation of the distribution of ammonia in animal houses). These studies have reinforced that although indoor concentrations may be acceptable near the height of the worker, the concentration at the height of the birds is often much higher and can drive decreased bird performance.

Traditional ventilation systems are not focused on gaseous pollutant removal, e.g., for ammonia. As previously mentioned, traditional pollutant removal occurs in conjunction with ventilation, initiated by temperature limits. Therefore, their main purpose is not on reducing pollutant concentrations which can cause a buildup of pollutants, especially with reused litter and lower ventilation periods found during brooding and cooler weather.

Existing technologies that attempt to solve this issue include biofilters, biotrickling filters, acid scrubbers, litter additives, a bubble column reactor, and a passive permeable membrane system.

Biofilters utilize packed, porous beds of an organic medium, such as compost, which are immobilized on a metal sieve. The flue gas is passed through the packed bed where nitrifying microorganisms on the material convert the ammonia to harmless nitrates. The system utilizes the existing ventilation fans and solely treats exhausted emissions, which means ammonia capture is reduced during low ventilation periods and the system cannot improve indoor air quality. Their performance highly depends on residence times within the material, maintenance of the microorganisms, and control of moisture levels. They often experience degraded performance with high ammonia and dust levels which are found with poultry houses. Biofilters are typically not considered viable for long-term filtration needs due to rapid microorganism exhaustion from pollutant concentrations found in poultry production. They also require a high material surface area to air flow, necessitating a large equipment requirement (Melse, Ogink, & Rulkens, W. H. (2009). Air Treatment Techniques for Abatement of Emissions from Intensive Livestock Production. The Open Agriculture Journal, 3, 6-12).

Biotrickling filters use a similar operating method as biofilters, namely nitrification of ammonia, but utilize an acidic trickle of water to increase performance. They are able to maintain higher efficiencies than biofilters, but also require long residence times which drives large equipment requirements. The filters are susceptible to the same clogging and performance degradations found with traditional biofilters, providing challenges with their use in poultry houses. Finally, pressure drop can increase up to 70 Pa during operations which is too great for traditional ventilation fans, thus necessitating the replacement of existing ventilation fans (Lahav, O., Mor, T., Heber, A. J., Molchanov, S., Ramirez, J. C, Li, C., & Broday, D. M. (2008). A New Approach for Minimizing Ammonia Emissions from Poultry Houses. *Water, Air, and Soil Pollution*, 191(1-4), 183497. doi:10.1007/s11270-008-9616-0). Like biofilters, biotricklers depend upon the existing ventilation infrastructure and are unable to affect the indoor air quality or filter ammonia when ventilation fans are not running.

Acid scrubbers utilize a tower packed with organic media that relies on water sprayed from the top with a low pH (<4) to cross-current or counter-contact the flue gas. The large amount of contact between the aqueous and gaseous fluids results in filtration of the pollutant. The device relies on the utilization of existing ventilation fans and must utilize a large contact area to maintain a low pressure drop to prevent additional energy use or require installation of additional fans. Byproducts of the system include concentrated ammonium salt and wastewater, which often require disposal. Variation in performance is experienced during high ventilation periods (superficial velocity is increased above 1.5 m/s) and when concentrations are high, which causes non-consistent performance. Furthermore, there is a large equipment cost due to the high surface area of packing material necessary to maintain residence time and low pressure drops (Lahav, O., Mor, T., Heber, A. J., Molchanov, S., Ramirez, J. C., Li, C., & Broday, D. M. (2008). A New Approach for Minimizing Ammonia Emissions from Poultry Houses. *Water, Air, and Soil Pollution*, 191(1-4), 183497. doi:10.1007/s11270-008-9616-0).

Litter additives to include chemical and microbial additives such as sodium bisulfate and aluminum sulfate can be added to the litter to either prevent ammonia formation or by neutralizing the ammonia through acidification. Performance is initially high (~75%) and then declines throughout the end of the cycle as the additive is used up. Additives must be continually added to maintain a high efficiency, but they provide diminishing returns since continual addition of additives are not possible during crops and are consumed at varying rates due to the variability in ammonia formation (Moore, P., Miles, D., & Burns, R. (2008). Reducing Ammonia Emissions from Poultry Litter with Alum. Mitigating Air Emissions from Animal Feeding Operations).

Another technique involves a bubble column reactor that utilizes an acidic solution to selectively target the air volume near the bird height. Air flow is provided to the reactor, containing a low pH acid solution, at a superficial velocity <0.04 m/s. Efficiency is near 100% at this flow velocity and requires replacement of the acid once exhausted. The reactor utilizes a separate ventilation system to decouple its operation from the main ventilation system to maintain low ammonia concentrations within the house. This technique allows for a decreased system size due to the smaller volumetric flow rate, however, the low superficial velocity still drives a large equipment size causing a significant challenge to its economic attractiveness (Lahav, O., Mor, T., Heber, A. J., Molchanov, S., Ramirez, J. C., Li, C., & Broday, D. M. (2008). A New Approach for Minimizing Ammonia Emissions from Poultry Houses. *Water, Air, and Soil Pollution*, 191(1-4), 183497. doi:10.1007/s11270-008-9616-0).

Another technique is the use of a microporous, hydrophobic, gas permeable membrane. The system is a passive system that pumps acid through tubing located near the height of the birds. Ammonia is allowed to pass through the membrane where it is then collected in a concentrated ammonium salt. It does not require any air flow handling and is thus able to reduce electricity costs (Szogi, A. A., Vanotti, M. B., & Rothrock, M. J. (2014). U.S. Pat. No. 8,906,332 B2. Washington, DC: U.S. Patent and Trademark Office.).

For at least these reasons, many problems and shortcomings exist with known technologies and processes.

SUMMARY

Some aspects of the invention relate to providing a system and method for overcoming some or a set of the problems set forth above simultaneously.

According to one aspect of some embodiments, the system and method provide for the filtration of one or more gaseous or solid pollutants (e.g., ammonia) from an agriculture (or other) facility, through the use of solid sorbents.

According to one aspect of some embodiments, the system and method are configured to both reduce atmospheric emissions from CAFOs and improve the indoor air quality of such operations to improve the health and performance of animals and the working environments for humans. Multiple systems can be integrated to filter any number of pollutants.

According to one aspect of some embodiments, the system and method involve use of a panel-bed system that utilizes solid adsorbents specifically chosen for their selectivity toward the desired pollutant (e.g., ammonia). The sorbents are arranged in vertical beds that are arranged horizontally to provide a compact footprint. High mass transfer rates found with sorbents allow for equipment size to be minimized. The sorbent is able to filter the pollutant when contacted with the flue gas described by physisorption and chemisorption principles. The sorbents are placed in thin beds to minimize the pressure drop and resulting electricity costs.

According to one aspect of some embodiments, the system and method involves the use of a customizable duct system, either indoor, outdoor, or a combination, to draw in air, independent of the main ventilation system, to deliver the air to the panel-bed for filtration of the pollutant from the air stream. Air is either recirculated into the structure or exhausted to the ambient environment.

According to one aspect of some embodiments, the system and method involve use of the targeted filtration of air inside the structure and independent of the main ventilation system, such that the indoor air quality can be improved to increase the animal performance. This also reduces the atmospheric emissions and reduces the environmental footprint of such operations.

According to one aspect of some embodiments, the system and method is configured and operable to produce a useable byproduct utilizing the captured pollutant to offset the cost of capture and increase the efficiency of the system.

According to another aspect of some embodiments, the system and method are configured and operable to provide a gaseous pollutant (e.g., ammonia) removal filtration device independent of the traditional (e.g., animal house) ventilation system to control emissions and simultaneously improve the health and wellbeing of workers and birds. The reduction of emissions can improve natural resources, prevent small particulate formation, and improve health and societal CAFO tolerance of local populaces. Such an approach can increase the weight and production of broilers, layers, and other animals to improve the economics of CAFOs. Additionally, the system may be located close to the surface of the litter and the origin of ammonia production to minimize the volumetric flow requirement and, therefore, the overall system size by targeting this air volume.

In contrast to some prior system, the various aspects of the disclosed system and method can simultaneously achieve multiple design goals and solve combinations of problems, including various permutations of the problems set forth above. The unique configuration and operation of the systems and methods described herein provides synergistic results not heretofore seen with prior systems.

For simplicity, various examples are provided in connection with ammonia capture from poultry CAFOs where the system can be coupled with a particulate matter filter device to reduce particulates for further emissions control and improved animal health. The invention is not limited to this specific example. The technology described herein can be used in other facilities and/or for other pollutants.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

Figure 1:
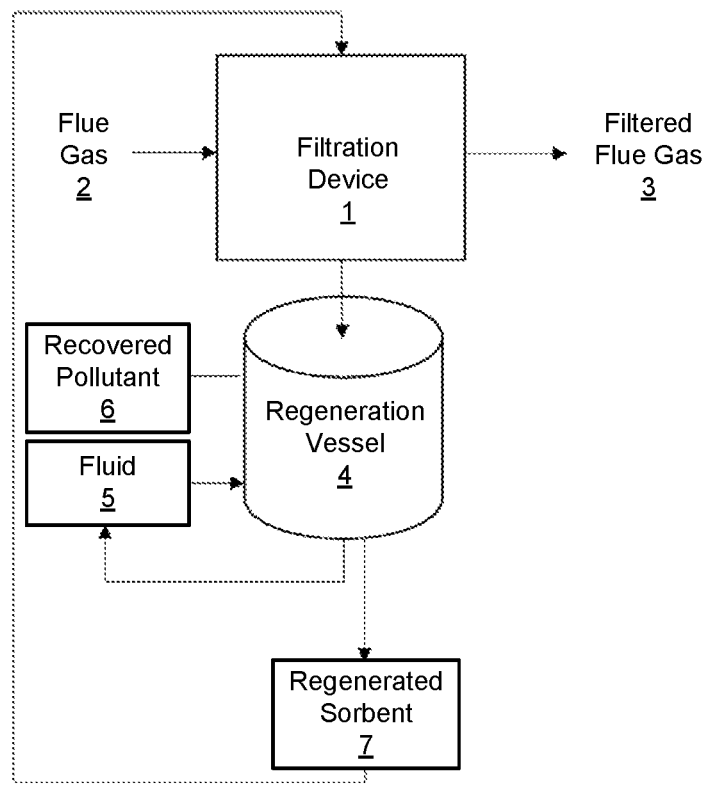
FIG. 1 is a block system diagram of a panel-bed pollutant capture system according to some embodiments of the disclosed technologies.

The figures are not exhaustive and do not limit the present disclosure to the precise form disclosed.

DETAILED DESCRIPTION

Embodiments of the disclosure provide systems and methods for the capture of gaseous and/or solid pollutants from an enclosed area. The gaseous pollutants may include ammonia, carbon dioxide, and similar gaseous pollutants. Solid pollutants may include any size of particulate matter. The source of the pollutants may be within the enclosed area. The source of the pollutants may be waste from concentrated feeding animal operations or other sources. In this disclosure, the animals are sometimes described as poultry. However, is should be understood that the disclosed technologies apply to animals other than poultry as well.

The system may collect polluted air through one or more air filtration devices, such as a series of ducts for filtration in a panel-bed device that may use solid sorbents placed in vertical beds arranged horizontally in a compact system. Each panel consists of two mesh screens that are separated by a distance equivalent to the desired sorbent bed depth, typically less than one inch. Each mesh is supported by a rectangular frame that is used to provide structure and tension to the mesh. The mesh forms the filtration area of the unit and permits air to pass through the system and contact the sorbent to effect filtration. The sorbents are placed in the middle of each panel and are delivered from the top of the unit and expulsed at the bottom. Together, the sorbent and panel form the panel-bed. Each vertical panel is placed into the main chassis, and additional panels are arranged horizontally to scale the unit to the required capacity. The total surface area of the contact side of the panels is directly proportional to the volumetric flow capacity of the system. Each panel is segregated from the others by non-porous barriers on either side to form a panel-bed chamber, so air can be uniformly distributed across each panel. The air manifold is designed to deliver and remove uniformly distributed air to each panel-bed chamber for even saturation and efficient system operations. The collected pollutant may be recovered from the solid sorbents through a regeneration device that utilizes one or more recovery processes. The recovery process may include heat, pressure changes, fluid wash, and similar processes. The pollutant may be recovered in a gaseous or liquid form. The pollutant may be recovered in a manner that allows the reuse of the pollutant.

The solid sorbents may include zeolites, activated carbon, ion exchange resins, metal organic frameworks (MOFs), Prussian blue, and/or other solid sorbents. The gaseous pollutants may include any material or compound that can be adsorbed by sorbents.

The system may include multiple panel-beds of different sorbents for the removal of multiple pollutants. The system may be coupled with a particulate matter filter device to reduce particulates for further emissions control and improved animal health.

The disclosed technologies may employ a panel-bed filtration system that utilizes thin vertical beds of solid sorbents. The sorbent beds may be thin, for example less than two inches in thickness, and typically less than one inch. Other thicknesses may be used. The thickness may be selected according to the characteristics of the sorbent employed. The thin sorbent bed depths allow for a short flow path which minimizes the pressure drop and required energy for system operations. The horizontally arranged vertical beds permit a small footprint to be maintained and for equipment sizes and capital costs to be minimized. Bed thickness selection is dependent on the adsorption equilibrium capacity of each sorbent at the pollutant partial pressure found within the flue gas. This instantaneous pollutant concentration directly corresponds to a capacity of that pollutant in the sorbent, and the capacity can change due to any number of factors including temperature, humidity, variation in pollutant partial pressures, and competing pollutants. The resulting capacity and pollutant concentration results in a specific saturation time in which the sorbents will need to be replaced. Utilizing these respective sorbent characteristics, the bed depth can be selected for the employed sorbent to achieve the desired process characteristics and performance, such as cycle time. Furthermore, factors such as superficial flow velocity and sorbent mass transfer limitations can affect the mass flow rate of pollutants, the capture efficiency, cycle time, and other process characteristics and must be accounted for when determining bed thickness. Optimizing these characteristics ensures an efficient system as together, the sorbent's capabilities, resulting air flow velocity, and total available filtration area provided by the panels affect the total size and performance of the device.

The system may draw in air from ventilation ducts placed at appropriate elevations throughout a broiler, layer, or other poultry facility. For example, the ducts may be placed along the feeder lines in a broiler house. The ducts may be customized to the specific needs of the facility and may also be placed outside of the building if needed. Air may be drawn into a central duct, e.g., via a high flow rate fan that leads to the panel-bed filter. The air flow rate may be approximately 10% of the house volume per minute. However, volumetric flow may be increased by adding additional panels to handle the desired air volume. An air manifold may receive and distribute the air flow among the enclosed and segregated vertical panel-beds to uniformly saturate the sorbent beds. The panel-bed may have a number of vertical panel-beds whose quantity is dependent on the size of the house, the resulting air flow requirement, and the desired superficial velocity. Superficial velocity is determined based upon the pollutant mass transfer rate of the sorbent. Each sorbent has a corresponding pollutant mass transfer rate limitation, and this rate can be affected by a number of factors (humidity, temperature, competing pollutants, etc.). The flue gas will have a varying mass flow rate based upon pollutant formation rates, resulting animal structure concentrations, and volumetric flow velocity. The superficial flow velocity is selected based upon ensuring the mass flow rate does not exceed the mass transfer rate of the sorbent so a high capture efficiency can be maintained throughout filtration. Other factors that can affect the selected superficial flow velocity may include sorbent bed thickness, equipment costs, equipment limitations, and pressure drop limitations.

Superficial air velocity is dependent on the characteristics of the sorbent and can commonly range between 0.1 m/s to 2.0 m/s. The flue gas may pass through each sorbent bed where it contacts the solid sorbent and the desired pollutant is adsorbed to effect filtration, for example through physisorption and/or chemisorption. The flue gas may be filtered with high efficiency, up to 100%, with minimal residence times before exiting the panel-bed. During cold weather, the air may be recycled back to the structure to minimize heat loss and reduce propane heating costs. In the summer, the air may be vented to provide additional ventilation capacity.

The filtration system may be decoupled from the main ventilation system to improve the indoor air quality near the animals for increased production performance while simultaneously reducing emissions. The system may utilize a dedicated fan to either continuously or intermittently filter the air. The fan may be triggered when pollutant levels exceed a desired threshold.

When the sorbent is sufficiently saturated with the adsorbate (that is, saturated to a desired degree), gates may open at the bottom of the unit and the sorbent may be expulsed into a sorbent collection bin at the bottom of the panel-beds. The gate may then close, and a gate at the top of the panel-bed may open to allow fresh sorbent to flow into the panels where filtration is allowed to resume. In various embodiments, the system may employ any combination of top or bottom gate, or use none at all.

The expulsed sorbent may be directed into a sorbent regeneration chamber. For certain sorbents (i.e., activated carbons, zeolites, MOFs, etc.) the sorbent may be directed to a bulk solids heat exchanger or other heating element or process, coupled with a vacuum pump in some circumstances, where heat sufficient for the specific sorbent is applied to decrease the adsorption equilibrium causing the adsorbate to desorb. A vacuum pump may operate to pull a vacuum to assist with desorption and/or recover the gaseous pollutant. A thermal fluid such as steam or thermal oil may be heated and used in the bulk solids heat exchanger. The recovered gaseous pollutant may then pass through a condenser, if needed, to reduce water content and then may be stored in a gaseous or liquid form. After desorption is sufficient, the sorbent may be moved to the top of the panel-bed by a conveyor where it may be allowed to cool until needed for adsorption once again. The conveyor may be pneumatic or mechanical. With sorbents such as Prussian blue analogues, the regeneration device may be a water jet system where sufficient water is utilized to wash the sorbent and recover the adsorbate in an aqueous form. The recovered pollutant may be sold for industry use or utilized to offset costs. For example, ammonium hydroxide may be used as fertilizer, and ammonia gas may be used as an alternative fuel source.

The disclosed technologies may utilize solid sorbents which have been shown to maintain high capture efficiencies until breakthrough, even at low ammonia concentrations (<10 ppm), and can be continually regenerated and reused to lower operations costs (Takahashi, A., Minami, K., Noda, K., Sakurai, K., & Kawamoto, T. (2020). Trace Ammonia Removal from Air by Selective Adsorbents Reusable with Water. *ACS Applied Materials & interfaces,* 12(13), 15115-15119, doi:10.1021/acsami.9b22384).

FIG. 1 is a block system diagram of a panel-bed pollutant capture system according to some embodiments of the disclosed technologies. While embodiments of the disclosed pollutant capture systems are described in terms of poultry farming, it should be understood that embodiments of the disclosed pollutant capture systems may have other applications, both in other farming operations and in non-farming operations.

Referring to FIG. 1, a panel-bed air filtration device 1 may receive flue gas 2 from the poultry house where it may pass through one or more sorbent beds within the filtration device 1. The filtration system may capture one or more pollutants from the flue gas. At 3, the filtered flue gas may be recirculated to the poultry house, exhausted outside the poultry house, or a combination thereof. After the sorbents are saturated with the pollutant(s), they may be dropped into a regeneration vessel 4. A fluid 5 may be used to recover the pollutant(s). In some embodiments, thermal fluid may be used to regenerate the sorbent through heating, for example via a heat exchanger. In some embodiments, water may be sprayed into the tank to regenerate the sorbent. The recovered pollutant 6 may be removed from the regeneration vessel 4. A vacuum pump may be used to remove gaseous pollutants. A water pump may be used to remove aqueous pollutants. For particulate matter filtration, the device could be After regeneration, the regenerated sorbent 7 may be conveyed to the top of the panel-bed for reuse.

Figure 2:
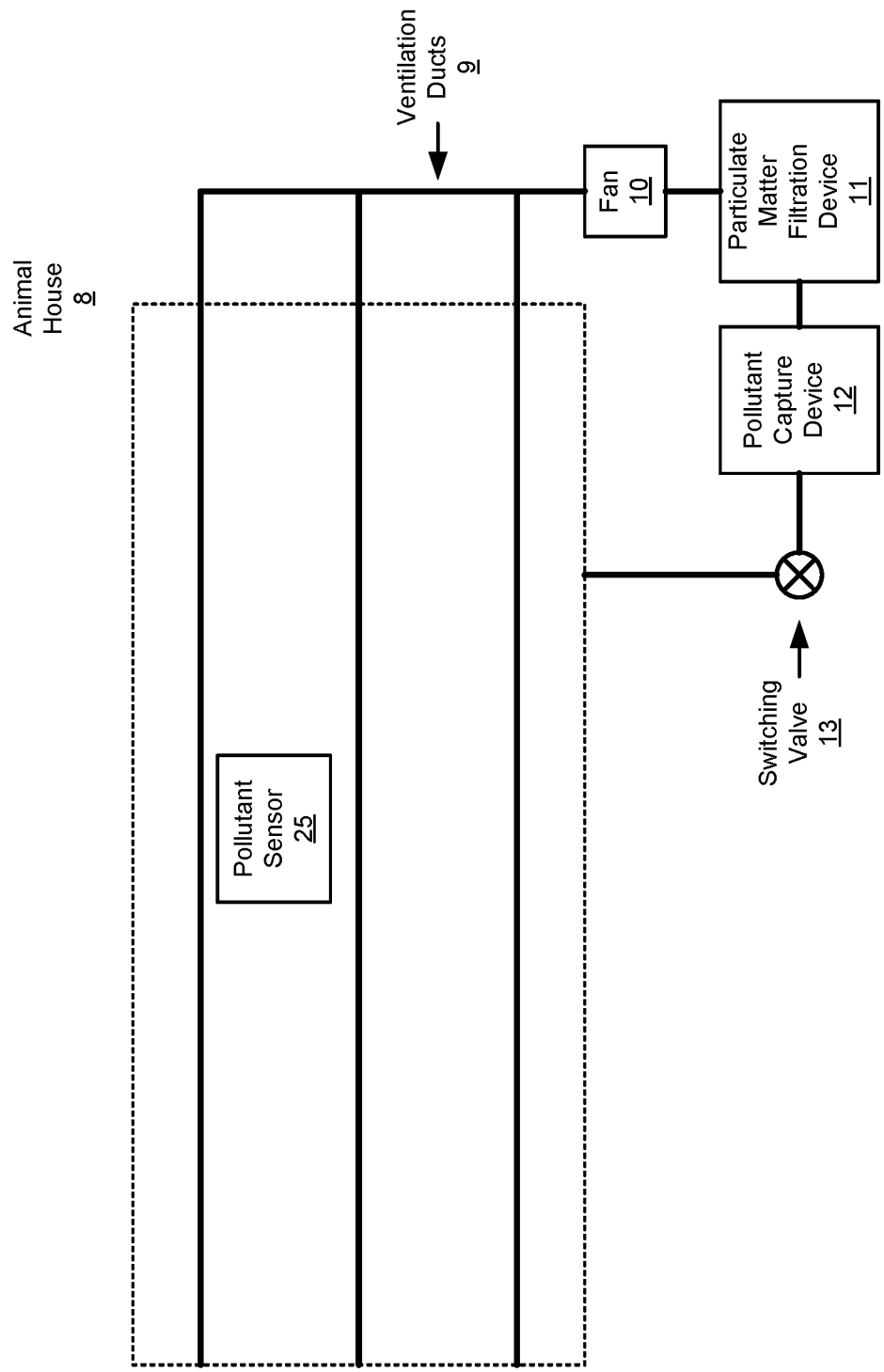
FIG. 2 depicts a complete filtration system according to some embodiments of the disclosed technologies.

FIG. 2 depicts a complete filtration system according to some embodiments of the disclosed technologies. Ventilation air ducts 9 may be placed within the enclosed area of the poultry house 8 at the same elevation as the birds. The ducts 9 may be attached to other structures, for example such as the feeding lines. A fan or blower 10 may draw in polluted air from the ducts, and may deliver the air to an optional particulate matter filtration device 11. The optional particulate matter filtration device 11 may be a bag filter, cartridge filter, or a similar device. The particulate matter filtration device may also be a panel-bed device that uses a sorbent, such as a silica, to effect capture of all particulate sizes. A particulate matter regeneration device such as a fluidized bed may be used to separate the sorbent from the particulate matter. The air may then be passed through a panel-bed pollutant capture device 12 where the pollutant may be filtered and recovered. The panel-bed pollutant capture device 12 may be implemented as shown in FIG. 1. The filtered air may then be recirculated to the poultry house, exhausted outside the poultry house, or a combination thereof, by a switching valve 13. A pollutant sensor 25 may be disposed within the poultry house 8 at the same elevation as the birds. The fan or blower 10 may be triggered when readings from the sensor 25 exceed a threshold.

Figure 3:
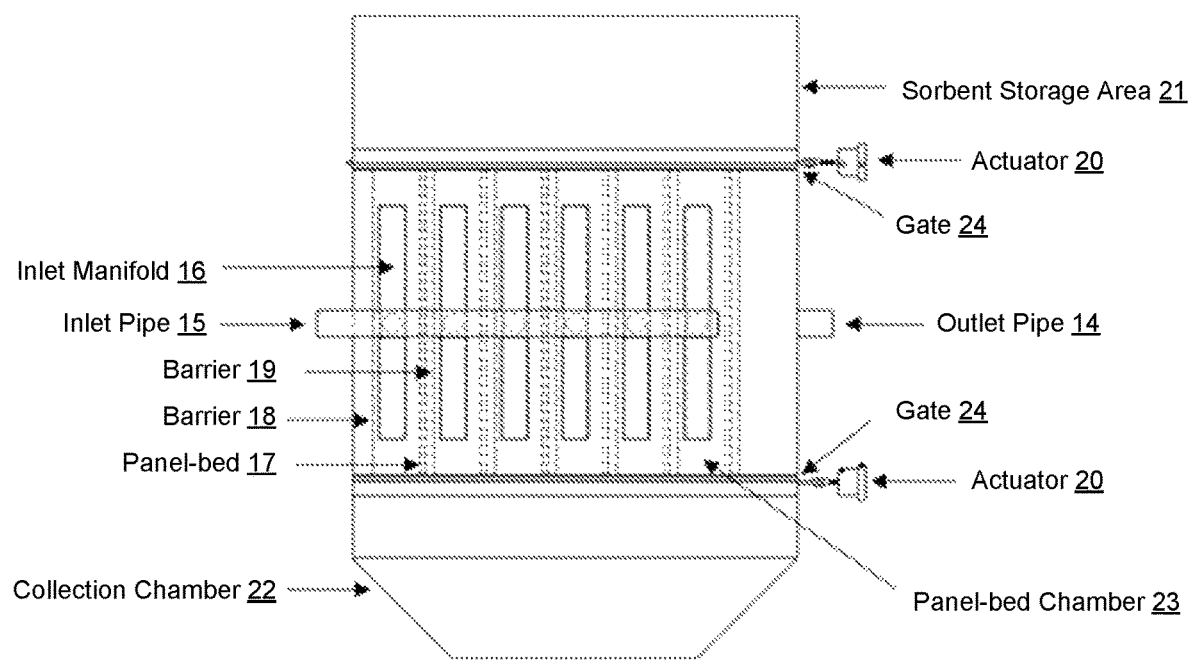
FIG. 3 shows a panel-bed filter according to some embodiments of the disclosed technologies.

FIG. 3 shows a panel-bed filter according to some embodiments of the disclosed technologies. Flue gas may enter an inlet pipe 15, and may be distributed equally within an inlet manifold 16. Each portion of the inlet manifold 16 may distribute the flue gas to a respective enclosed panel-bed chamber 23. Within each panel-bed chamber 23, the flue gas may pass through a respective panel-bed 17. Each panel-bed 17 may contain sold sorbent (not shown). In some embodiments, each panel-bed 17 may be less than 1 inch thick. Each panel-bed 17 may be enclosed by barriers 18, 19 on both sides to segregate the distributed air flow amongst all panel-beds. For example, each panel-bed 17 may be enclosed on both sides by a non-porous sheet or a similar device to form the panel-bed chambers 23. The flue gas may be distributed along the entire length of the panel-bed chamber 23 to promote uniform saturation of the solid sorbent. The filtered gas may exit each panel-bed 17 through outlet manifolds (not shown) and an outlet pipe 14. The outlet manifolds may be implemented in a manner similar to that of the inlet manifolds 16.

When the sorbents are saturated, a gate 24 at the bottom of the panel-bed filter may open to allow the saturated sorbent to fall into the collection chamber 22. The gate 24 may be closed, and a similar gate 24 at the top of the panel-bed filter may be opened to allow fresh sorbent to fill the panel-beds 17 from a sorbent storage area 21. The gates 24 may be operated via actuators 20. The saturated sorbents may then be sent from the collection chamber 22 to a regeneration section (not shown) to desorb and recover the pollutant. Regenerated sorbent may be conveyed to the sorbent storage area 21.

In the embodiment of FIG. 3, the vertical panel-beds 17 are arranged horizontally, and gravity alone may be sufficient to remove the saturated sorbents from the panel-beds 17. In other embodiments, the panel-beds 17 may be non-vertical and arranged in a non-horizontal manner. In any embodiment, a scraper may be used to affect the removal of the saturated sorbents from the panel-beds 17.

Figure 4:
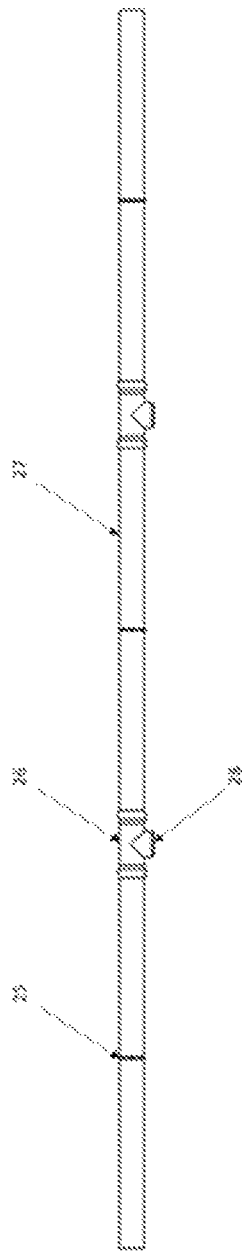
FIG. 4 provides an example duct pipe that may be placed inside an animal house for the targeted capture of a specific air volume.

FIG. 4 provides an example duct pipe 27 that may be placed inside an animal house for the targeted capture of a specific air volume. The duct pipe 27 may be attached to the feeding lines in a poultry house via a bracket 25. Couplings 26 may serve as duct inlets. Each coupling 26 may have a screen 28 to prevent large particulate matter from entering the duct inlet.

Figure 5:
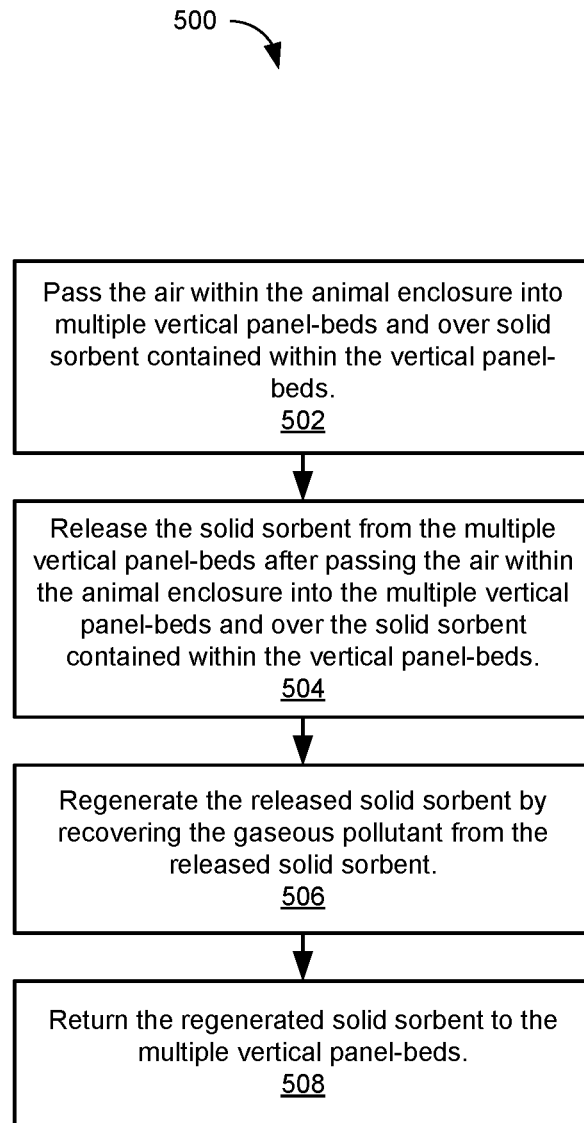
FIG. 5 is a flowchart illustrating a process for collecting a gaseous pollutant from air within an animal enclosure.

FIG. 5 is a flowchart illustrating a process 500 for collecting a gaseous pollutant from air within a poultry enclosure. The elements of the process 500 are presented in one arrangement. However, it should be understood that one or more elements of the process may be performed in a different order, in parallel, omitted entirely, and the like. Furthermore, the process 500 may include other elements in addition to those presented.

Referring to FIG. 5, the process 500 may include passing air within the poultry enclosure into multiple vertical panel-beds and over solid sorbent contained within the vertical panel-beds, at 502. For example, the blower 10 of FIG. 2 may pass air within the poultry enclosure 8 into the multiple vertical panel-beds 17 of FIG. 3 and over the solid sorbent contained within the vertical panel-beds 17.

Referring again to FIG. 5, the process 500 may include releasing the solid sorbent from the multiple vertical panel-beds after passing the air within the poultry enclosure into the multiple vertical panel-beds and over the solid sorbent contained within the vertical panel-beds, at 504. For example, referring again to FIG. 3, the actuator 20 may operate the outlet gate 24 to release the solid sorbent from the multiple vertical panel-beds 17 into the collection chamber 22.

Referring again to FIG. 5, the process 500 may include regenerating the released solid sorbent by recovering the gaseous pollutant from the released solid sorbent, at 508. For example, the released solid sorbent may be conveyed from the collection chamber 22 of FIG. 3 to the regeneration vessel 4 of FIG. 1. The solid sorbent may be regenerated as described above, and the recovered gaseous pollutant may be collected, as shown at 6 in FIG. 1.

Referring again to FIG. 5, the process 500 may include returning the regenerated solid sorbent to the multiple vertical panel-beds, at 510. For example, referring again to FIG. 1, the regenerated solid sorbent may be conveyed from the regeneration vessel 4 to the panel-bed air filtration device 1. Referring again to FIG. 3, the regenerated solid sorbent may be conveyed to the sorbent storage area 21. The actuator 20 may operate the inlet gate 24 to release the solid sorbent into the multiple vertical panel-beds 17 from the sorbent storage area 21 into the collection chamber 22.

Embodiments of the disclosed technologies may be implemented to provide advantages over conventional solutions. The disclosed technologies both reduce atmospheric emissions from CAFOs, and improve the indoor air quality of such operations to improve the health and performance of animals and the working environments for humans. The arrangement of the sorbents in vertical beds that are horizontally stacked provide a compact footprint, for example having sizes magnitudes smaller than traditional technologies. The sorbents may be placed in thin beds to minimize the pressure drop and resulting electricity costs. The customizable duct system may be independent of the main ventilation system to provide a dedicated system for the removal of pollutants, and so air may be recirculated into the structure, exhausted to the ambient environment, or both. The system may produce a useable byproduct utilizing the captured pollutant, which may offset the cost of capture and increase the economics of the system.

Figure 6:
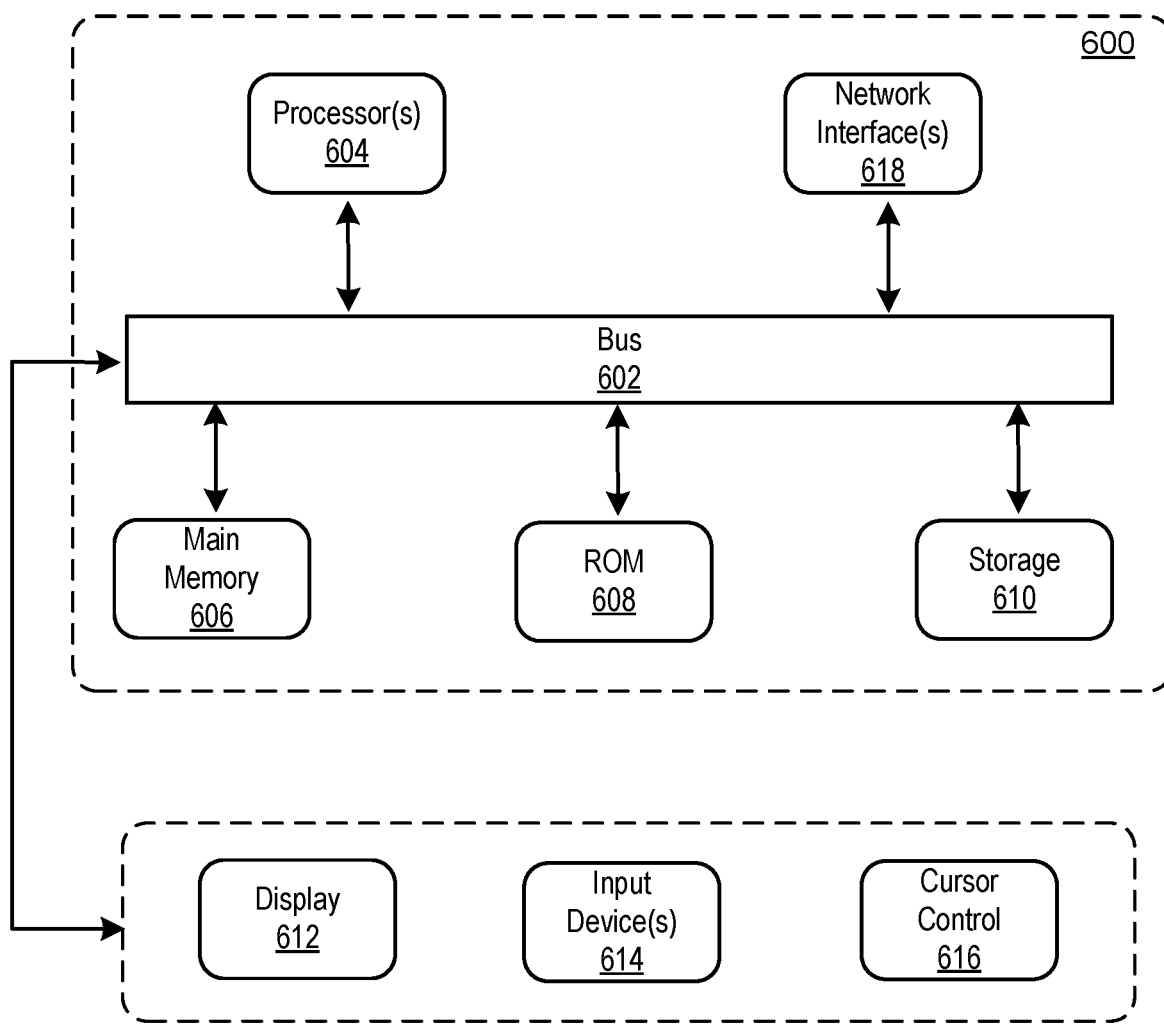
FIG. 6 is an example computing component that may be used to implement various features of embodiments described in the present disclosure.

In some embodiments, the operation of the disclosed systems may be controlled by a computer system. FIG. 6 depicts a block diagram of an example computer system 600 in which embodiments described herein may be implemented. The computer system 600 includes a bus 602 or other communication mechanism for communicating information, one or more hardware processors 604 coupled with bus 602 for processing information. Hardware processor(s) 604 may be, for example, one or more general purpose microprocessors.

The computer system 600 also includes a main memory 606, such as a random access memory (RAM), cache and/or other dynamic storage devices, coupled to bus 602 for storing information and instructions to be executed by processor 604. Main memory 606 also may be used for storing temporary variables or other intermediate information during execution of instructions to be executed by processor 604. Such instructions, when stored in storage media accessible to processor 604, render computer system 600 into a special-purpose machine that is customized to perform the operations specified in the instructions.

The computer system 600 further includes a read only memory (ROM) 608 or other static storage device coupled to bus 602 for storing static information and instructions for processor 604. A storage device 610, such as a magnetic disk, optical disk, or USB thumb drive (Flash drive), etc., is provided and coupled to bus 602 for storing information and instructions.

The computer system 600 may be coupled via bus 602 to a display 612, such as a liquid crystal display (LCD) (or touch screen), for displaying information to a computer user. An input device 614, including alphanumeric and other keys, is coupled to bus 602 for communicating information and command selections to processor 604. Another type of user input device is cursor control 616, such as a mouse, a trackball, or cursor direction keys for communicating direction information and command selections to processor 604 and for controlling cursor movement on display 612. In some embodiments, the same direction information and command selections as cursor control may be implemented via receiving touches on a touch screen without a cursor.

The computing system 600 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "component," "engine," "system," "database," data store," and the like, as used herein, can refer to logic embodied in hardware or firmware, or to a collection of software instructions, possibly having entry and exit points, written in a programming language, such as, for example, Java, C or C++. A software component may be compiled and linked into an executable program, installed in a dynamic link library, or may be written in an interpreted programming language such as, for example, BASIC, Perl, or Python. It will be appreciated that software components may be callable from other components or from themselves, and/or may be invoked in response to detected events or interrupts. Software components configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware components may be comprised of connected logic units, such as gates and flip-flops, and/or may be comprised of programmable units, such as programmable gate arrays or processors.

The computer system 600 may implement the techniques described herein using customized hard-wired logic, one or more ASICs or FPGAs, firmware and/or program logic which in combination with the computer system causes or programs computer system 600 to be a special-purpose machine. According to one embodiment, the techniques herein are performed by computer system 600 in response to processor(s) 604 executing one or more sequences of one or more instructions contained in main memory 606. Such instructions may be read into main memory 606 from another storage medium, such as storage device 610. Execution of the sequences of instructions contained in main memory 606 causes processor(s) 604 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 610. Volatile media includes dynamic memory, such as main memory 606. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 602. Transmission media can also take the form of acoustic or light waves, such as those generated during radio-wave and infra-red data communications.

The computer system 600 also includes a communication interface 618 coupled to bus 602. Network interface 618 provides a two-way data communication coupling to one or more network links that are connected to one or more local networks. For example, communication interface 618 may be an integrated services digital network (ISDN) card, cable modem, satellite modem, or a modem to provide a data communication connection to a corresponding type of telephone line. As another example, network interface 618 may be a local area network (LAN) card to provide a data communication connection to a compatible LAN (or a WAN component to communicate with a WAN). Wireless links may also be implemented. In any such implementation, network interface 618 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world wide packet data communication network now commonly referred to as the "Internet." Local network and Internet both use electrical, electromagnetic or optical signals that carry digital data streams. The signals through the various networks and the signals on network link and through communication interface 618, which carry the digital data to and from computer system 600, are example forms of transmission media.

The computer system 600 can send messages and receive data, including program code, through the network(s), network link and communication interface 618. In the Internet example, a server might transmit a requested code for an application program through the Internet, the ISP, the local network and the communication interface 618.

The received code may be executed by processor 604 as it is received, and/or stored in storage device 610, or other non-volatile storage for later execution.

Each of the processes, methods, and algorithms described in the preceding sections may be embodied in, and fully or partially automated by, code components executed by one or more computer systems or computer processors comprising computer hardware. The one or more computer systems or computer processors may also operate to support performance of the relevant operations in a "cloud computing" environment or as a "software as a service" (SaaS). The processes and algorithms may be implemented partially or wholly in application-specific circuitry. The various features and processes described above may be used independently of one another, or may be combined in various ways. Different combinations and sub-combinations are intended to fall within the scope of this disclosure, and certain method or process blocks may be omitted in some implementations. The methods and processes described herein are also not limited to any particular sequence, and the blocks or states relating thereto can be performed in other sequences that are appropriate, or may be performed in parallel, or in some other manner. Blocks or states may be added to or removed from the disclosed example embodiments. The performance of certain of the operations or processes may be distributed among computer systems or computers processors, not only residing within a single machine, but deployed across a number of machines.

As used herein, a circuit might be implemented utilizing any form of hardware, or a combination of hardware and software. For example, one or more processors, controllers, ASICs, PLAs, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. Even though various features or elements of functionality may be individually described or claimed as separate circuits, these features and functionality can be shared among one or more common circuits, and such description shall not require or imply that separate circuits are required to implement such features or functionality. Where a circuit is implemented in whole or in part using software, such software can be implemented to operate with a computing or processing system capable of carrying out the functionality described with respect thereto, such as computer system 600.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

What is claimed is:

1. An apparatus for collecting a gaseous pollutant from air, the apparatus comprising:
   a duct having a duct inlet in fluid communication with the air;
   an inlet pipe in fluid communication with (1) the duct and (2) an inlet manifold via multiple portions of the inlet manifold;
   multiple vertical panel-beds each containing a solid sorbent wherein the multiple vertical panel-beds are separately in fluid communication with the inlet manifold; and
   a fan configured to pass the air through the duct, the inlet pipe, and the inlet manifold into the multiple vertical panel-beds and over the solid sorbent.

2. The apparatus of claim 1, further comprising:
   an outlet manifold separately in fluid communication with the multiple vertical panel-beds to allow filtered air to exit the multiple vertical panel-beds after the fan passes the air through the duct and the inlet manifold into multiple vertical panel-bed chambers and over the solid sorbent.

3. The apparatus of claim 2, further comprising:
a regeneration vessel configured to regenerate a released solid sorbent by recovering the gaseous pollutant from the released solid sorbent.

4. The apparatus of claim 3, further comprising:
a conveyor configured to return the regenerated solid sorbent to the multiple vertical panel-beds.

5. The apparatus of claim 1, wherein the solid sorbent comprises at least one of:
a zeolite;
activated carbon;
an ion exchange resins;
a metal organic framework;
silica;
polymers;
amine functionalized sorbent variations;
Prussian blue; and
other natural organic, inorganic, or synthetic sorbents.

6. The apparatus of claim 1, wherein the gaseous pollutant comprises at least one of:
ammonia;
methane;
hydrogen sulfide;
nitrous oxides;
carbon monoxide; and
carbon dioxide.

7. The apparatus of claim 1, wherein each of the multiple vertical panel-beds comprises:
a porous sheet configured to contain the solid sorbent and non-porous sheets to enclose the vertical panel-beds.

8. The apparatus of claim 2, further comprising:
an actuator configured to operate an outlet gate configured to release the solid sorbent from the multiple vertical panel-beds after the fan passes the air through the duct and the inlet manifold into multiple vertical panel-bed chambers and over the solid sorbent.

9. The apparatus of claim 2, further comprising:
a collection chamber configured to hold the solid sorbent after release of the solid sorbent from the multiple vertical panel-beds.

10. The apparatus of claim 3, further comprising:
a sorbent storage area configured to hold the solid sorbent after transfer of the solid sorbent from the regeneration vessel; and
an inlet gate configured to release the solid sorbent from the sorbent storage area into the multiple vertical panel-beds.

11. The apparatus of claim 10, further comprising:
an actuator configured to operate the inlet gate.

12. The apparatus of claim 1, further comprising:
a particulate matter filtration device configured to filter particulates from the air prior to the air passing over the solid sorbent.

13. The apparatus of claim 1, further comprising:
a scraper configured to effect removal of the solid sorbent from the multiple vertical panel-beds.

14. The apparatus of claim 1, further comprising:
a screen configured to prevent large particulate matter from entering the duct inlet.

15. The apparatus of claim 1, wherein:
wherein two or more of the vertical panel-beds contain different solid sorbents to adsorb different gaseous pollutants.

16. The apparatus of claim 1, wherein the air enters the inlet pipe from one side of the apparatus and exits an outlet pipe on the other side of the apparatus.

17. The apparatus of claim 1, wherein each of the multiple vertical panel-beds is enclosed on both sides by a non-porous barrier to form a vertical panel-bed chamber.

18. The apparatus of claim 1, wherein each of the multiple vertical panel-beds is less than 1 inch thick.

19. The apparatus of claim 1, wherein the multiple vertical panel-beds are segregated.

* * * * *